United States Patent [19]

Platt, Jr.

[11] 4,304,928

[45] Dec. 8, 1981

[54] 2-ALKOXYACRYLATE PROCESS

[75] Inventor: James L. Platt, Jr., Novato, Calif.

[73] Assignee: Chevron Research Company, San Francisco, Calif.

[21] Appl. No.: 141,736

[22] Filed: Apr. 18, 1980

[51] Int. Cl.$^3$ .......................................... C07C 67/327
[52] U.S. Cl. ................................................... 560/183
[58] Field of Search ......................................... 560/183

[56] References Cited

U.S. PATENT DOCUMENTS 2,440,092  4/1948  Hyman et al. ...................... 560/183
2,571,212  10/1951  Croxall et al. ...................... 560/183

OTHER PUBLICATIONS

Claisen, L. *Berichte*, vol. 31 (1898) pp. 1019–1021.
Bordwell, F. et al. *J. Am. Chem. Society*, vol. 97, (1975) pp. 7006–7014.
Pearson, Ralph G. et al. *J. Am. Chem. Society* vol. 75 (1953) pp. 2439–2443.
House, H. O. "Modern Synthetic Reactions" (1965) Benjamin Press, Publ. p. 164.
Cram, Donald J. "Fundamentals of Carbanion Chemistry" (1965) Academic Press, Publ. p. 19.

*Primary Examiner*—Natalie Trousof
*Assistant Examiner*—L. Hendriksen
*Attorney, Agent, or Firm*—D. A. Newell; T. G. DeJonghe; C. J. Caroli

[57] ABSTRACT

This invention relates to a process for producing 2-alkoxyacrylate by heating an alkyl 2,2-dialkoxypropionate with a molar amount each of a heterocyclic amine and an organic carboxylic acid halide in the presence of a catalytic amount of an inorganic base.

7 Claims, No Drawings

2-ALKOXYACRYLATE PROCESS

BACKGROUND OF THE INVENTION

This invention is concerned with a new process for the production of an 2-alkoxyacrylate. In particular, the process involves the conversion of an alkyl 2,2-dialkoxypropionate into an alkyl-2-alkoxyacrylate by treatment with an acid chloride and an amine in the presence of a catalytic amount of an inorganic base.

PRIOR ART

The first member of the 2-alkoxyacrylate series, namely, methyl 2-methoxyacrylate, has been made by a rather involved process [J. W. Baker, J. Chem. Soc. 1942, 520 and modified by N. Ogata, et al., Bull. Chem. Soc., Japan 43, 2987 (1970)]. In this prior art process, acetaldehyde and methanol are reacted in the presence of HCl to produce 3-chloro-2-oxabutane which in turn is brominated to 3,4-dibromo-2-oxabutane. Reaction of this dibromide with copper cyanide gives β-bromo-α-methoxypropionitrile. Reaction with HCl and methanol, followed by heating converts this compound into the ester, namely methyl β-bromo-α-methoxypropionate. Dehydrobromination with piperidine leads to methyl 2-methoxyacrylate which upon treatment with ammonia produces the amide.

Methyl 2-methoxyacrylate has also been obtained from methyl 2,2-dimethoxypropionate by treatment with $P_2O_5$ [K. Von Auwers, Berichte 44, 3523 (1911)]. The methyl 2,2-dimethoxypropionate, in turn, was obtained from the condensation of methyl pyruvate with trimethylorthoformate. The ethyl ester of 2-ethoxyacrylic acid was made by heating ethyl 2,2-diethoxypropionate in the presence of $P_2O_5$ [L. Claisen, Berichte 31, 1019 (1898)]. The same reference teaches heating acetals in the presence of an acid chloride and a tertiary amine to produce an unsaturated ether and the corresponding alcohol.

Alkyl 2-alkoxyacrylates can be polymerized to useful polymers, and they are also useful as intermediates in the production of the corresponding 2-alkoxyacrylamides by reaction with ammonia. These unsaturated amides are readily polymerized to produce water-soluble polymers. Aqueous solutions of poly(2-alkoxy)acrylamide are useful in enhanced oil recovery processes.

STATEMENT OF THE INVENTION

Alkyl 2-alkoxyacrylate can be produced from alkyl 2,2-dialkoxypropionate by an improved process which comprises heating a reaction mixture of alkyl 2,2-dialkoxypropionate, a molar amount each of a heterocyclic amine and of an organic carboxylic acid halide in the presence of a catalytic amount of an inorganic base. Though not necessary, also present in the reaction is a small but effective amount of a phenolic polymerization inhibitor to ensure that polymerization of the product alkyl-2-alkoxyacrylate is minimized. The reaction using 2,2-dimethoxypropionate, acetyl chloride and pyridine as representative, proceeds as follows:

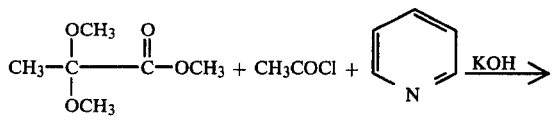

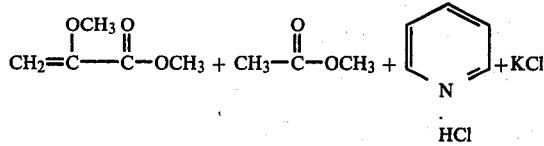

The alkyl 2,2-dialkoxypropionates useful as starting materials in carrying out the invention have the chemical structure:

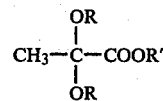

wherein R is an alkyl group of one to 12, preferably one to six carbon atoms, and R' is an alkyl group of 1 to 6 carbon atoms. Typical alkyl groups of 1 to 6 carbon atoms include methyl, ethyl, propyl, hexyl, 4-methyl pentyl, 2-methyl propyl, etc. Typical alkyl groups of 7 to 12 carbon atoms include heptyl, vinyl, decyl, dodecyl, 2-ethyl hexyl, etc. Representative compounds include ethyl 2,2-dipentoxypropionate, isopropyl 2,2-didodecoxypropionate, t-butyl 2,2-di(2-ethylhexoxy)-propionate, and the like. The preferred compound is methyl 2,2-dimethoxypropionate.

The conversion process of the invention is carried out by heating the starting materials to a temperature within about the range 50°–250° C., preferably about 100°–200° C. At these temperatures, the reaction time is usually about 15–120 minutes, the shorter times being at the higher temperatures. Atmospheric as well as superatmospheric pressures may be employed. When superatmospheric pressures are employed, pressures in about the range 15 to 115 psig will be found satisfactory.

The heterocyclic amines useful in the process are the nitrogen-containing unsaturated heterocyclic ring compounds having 5 carbons in the nitrogen-containing ring. These compounds have the chemical formula:

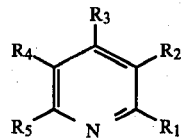

wherein $R_1$, $R_2$, $R_3$, $R_4$, and $R_5$ are independently hydrogen or an alkyl group of 1 to 4 carbon atoms or wherein any two adjacent R groups may represent a 3 or 4 carbon bridge forming a saturated or unsaturated, five- or six-membered ring fused to the nitrogen-containing ring. Representative heterocyclic amine bases include pyridine, picolines (methyl pyridines), lutidines (dimethyl or ethyl pyridines), collidines (ethyl methyl pyridines, trimethyl pyridines, and propyl pyridines), quinoline, iso-quinoline, methyl substituted quinolines, acridine, phenanthridine, 5,6,7,8-tetrahydroquinoline, 5,6,7,8-tetrahydroisoquinoline, and the like. The preferred heterocyclic amine base is quinoline.

The acid halide useful in the reaction has the chemical structure:

wherein R is a hydrocarbyl radical of 1 to 12 carbon atoms and X is a halogen. Preferably X is chlorine. The hydrocarbyl radical includes both aliphatic and aromatic species. Typical radicals exemplifying R are methyl, ethyl, hexyl, 2-ethylhexyl, nonyl, dodecyl, phenyl, tolyl xylyl, isopropylphenyl, 2-phenylethyl, 4-phenyloctyl, naphthyl, and the like. Specific acid halides include acetyl chloride, propionyl chloride, acetyl bromide, benzoyl chloride, 4-methyl benzoyl chloride, phenacetyl chloride, 4-phenyl-butyroyl chloride, 2-naphthoyl chloride, etc. The preferred compound is cinnamoyl chloride.

The catalyst for the reaction is a strong inorganic base. Those bases having a $pK_b$ value less than 5, preferably less than 3, are good catalysts for this reaction. These include the alkali metal and alkaline earth metal hydroxides and ammonium hydroxide. Typical bases include sodium hydroxide, magnesium hydroxide, and the like. Potassium hydroxide is the preferred catalyst.

The strong inorganic base is used in catalytic quantities. Thus the amount of this base to be employed is in about the range of 0.001 mols to 0.1 mols, preferably 0.005 to 0.01 mols for each mol of the heterocyclic amine base.

In one embodiment of the invention all the reactants namely, 2,2-dialkoxypropionate, heterocyclic amine, acid chloride, and inorganic base may be charged to the reaction vessel at one time, and the reaction mixture subjected to reaction conditions.

In another embodiment of the invention, the process is carried out by charging a reactor with the alkyl 2,2-dialkoxypropionate, a molar amount of the heterocyclic amine base, and a catalytic amount of the strong, inorganic base. Then the acid halide is added slowly and the entire mixture heated at a temperature in the range of 50°–200° C. until the reaction is complete. In this mode of operation it is desirable to purge the system with some inert gas, e.g., nitrogen or carbon dioxide prior to the addition of the acid halide. The 2-alkoxyacrylate is isolated from the reaction mixture by distillation.

Alternatively, a solvent, e.g., ethyl ether or a hydrocarbon, can be added to precipitate the heterocyclic amine hydrohalide co-product. This precipitate is removed by filtration, and the filtrate is distilled to give the acrylate product as one of the overhead fractions. Preferably, distillations are carried out under reduced pressure.

In the preferred mode of operation, near equal molar amounts of methyl 2,2-dimethoxypropionate and quinoline, along with 0.05 of a molar amount of potassium hydroxide, are charged to the reactor. Then a molar amount of cinnamoyl chloride is added slowly after the system has been purged with nitrogen, whereupon the mixture is heated at about 150° C. for about one hour. After cooling, the reaction mix is distilled at about 10 torr to give good yields of methyl 2-methoxyacrylate.

Also, to inhibit polymerization of the product 2-alkoxyacrylate, in the preferred mode of operation a polymerization phenolic inhibitor, e.g., hydroquinone or butylated hydroxy toluene is caused to be present in the reaction mixture. Suitable amounts of polymerization inhibitor range from about 0.02 to 2.0, preferably 0.1 to 0.4 weight percent of the methyl 2,2-dimethoxypropionate employed.

The starting material for the inventive process is easily obtained by the condensation of an alkyl pyruvate, e.g., methylpyruvate, with an alkyl orthoformate, e.g., trimethylorthoformate, preferably in the presence of an acid catalyst, e.g., ammonium chloride [K. Von Auwers, Ber., 44, 3523 (1911)].

EXPERIMENTAL

General

Methyl pyruvate, trimethyl orthoformate, quinoline, carboxylic acid chlorides, potassium hydroxide, and ammonium hydroxide were purchased as reagent grade materials. They were used without further purification unless indicated otherwise. NMR spectra were recorded on a Varian T-60 spectrometer in deuterochloroform and signals are reported downfield from tetramethylsilane unless otherwise indicated. Melting points were obtained in a Mel-Temp capillary tube apparatus and are corrected. Infrared spectra were recorded on a Perkin Elmer 337 spectrophotometer.

Reactions were monitored by gas chromatography (HP 5730A-FID chromatograph) using a 56-in. by ⅛-in. column 10% OV-101 30/100 DMCS. Relative retention times were methyl pyruvate < methyl 2-methoxyacrylate < methyl 2,2-dimethylpropionate <2-methoxyacrylamide.

The methyl 2,2-dimethoxypropionate used in the examples was prepared as follows: Methyl pyruvate (36 g, 0.35 mol), methanol (180 ml) and ammonium chloride 2 g (0.037 mol) were combined in a three-necked flask equipped with a dropping funnel, mechanical stirrer, thermometer, and distillation apparatus. Tri-methyl orthoformate (56 g, 0.53 mol) was added dropwise at 22°–25° C. The resulting solution was heated to boiling (65° C.) and methyl formate removed by distillation as it formed. Methanol was added to the reaction vessel as needed to maintain a 180-250 ml volume.

After nine hours, gas chromatography and NMR indicated methyl 2,2-propionate formation was greater than 95% complete. Solvent was evaporated in vacuo and the resultant yellow oil distilled to yield methyl 2,2-propionate (27.4 g, 53%); bp 32°–35° C. (4 torr) (lit 59°/11 torr), NMR, 1.46δ(s, 3H, $CH_3$); 3.22δ(s, 6H, $OCH_3$); and 2.75δ(s,3H, $CO_2CH_3$); IR, 1740 $cm^{-1}$ (CO).

EXAMPLE 1

Methyl 2,2-dimethoxypropionate (42.4 g, 0.29 mol), quinoline (38.7 g, 0.30 mol) (stored over potassium hydroxide), and hydroquinone (0.1 g) were placed in a three-necked flask; and the system purged with nitrogen. Benzoyl chloride (42.2 g, 0.30 mol) was added dropwise at 23°–24° C. The flask was heated to 100° C. over a 30 minute period. Conversion of methyl 2,2-dimethoxypropionate to methyl 2-methoxyacrylate was not detectable by NMR. After an additional 20 minutes at 127° C., conversion was 6%. After an additional 20 minutes, conversion remained at 6%.

Then while still at 127° C., powdered potassium hydroxide (0.35 g, 0.006 mol) was added in one portion. There was an immediate exotherm to 135° C. In less than 40 minutes, conversion of methyl 2,2-dimethoxypropionate to methyl 2-methoxyacrylate was greater than 99%.

The reaction mix was cooled to 65° C. and toluene added to precipitate quinoline hydrochloride. The slurry was cooled to 20°-25° C. and solids collected by filtration. The filtrate was concentrated in vacuo and distilled to yield methyl 2-methoxyacrylate (23.5 g, 70%); bp 43 (6 torr) (lit. 55° C., 10 torr) NMR, 3.60δ(s, 3H, OCH$_3$); 3.78δ(s, 3H, CO$_2$CH$_3$), 4.60δ(d, J=2 Hz, 1H, =CH) and 5.35δ(d, J=2 Hz, 1H, =CH); IR, 1730 cm$^{-1}$ (CO). As can be seen from this example, the inorganic base catalyst is essential in producing the methyl 2-methoxyacrylate product in good yields.

EXAMPLE 2

The procedure of Example 1 was repeated using methyl 2,2-dimethoxypropionate (487.7 g, 3.3 mols), cinnamoyl chloride (662.7 g, 4.0 mols), quinoline (513.8 g, 4.0 mols), and powdered potassium hydroxide (9.9 g, 0.18 mol). Over 70 minutes, the reaction mix was heated to 156° C., at which time product formation was complete. The yield of distilled methyl 2-methoxyacrylate was 306.5 g (80%): NMR and IR spectra were identical to that reported in Example 1.

EXAMPLE 3

The method of Example 1 was followed except cinnamoyl chloride replaced benzoyl chloride. Yield of distilled methyl 2-methoxyacrylate was 75%.

EXAMPLE 4

The method of Example 1 was followed except phthaloyl chloride replaced benzoyl chloride. Yield of distilled methyl 2-methoxyacrylate was 68%.

EXAMPLE 5

Methyl 2,2-dimethoxypropionate (66.9 g, 0.45 mol), hydroquinone (0.1 g), quinoline (74.5 g, 0.58 mol) (dried over potassium hydroxide), and acetyl chloride (48.4 g, 0.62 mol) were combined at 5°-10° C. in a Fischer-Porter bottle. Powdered potassium hydroxide (0.45 g, 0.008 mol) was added. The reaction mix formed a thick white slurry. The bottle was sealed, stirred with a magnetic stirrer, and placed in a 122° C. oil bath. After three hours the bottle pressure was 19–22 psig. The reaction mixture was diluted with toluene and the quinoline hydrochloride was removed by filtration. The filtrate was concentrated and distilled to give methyl 2-methoxyacrylate (35 g, 68%): bp 35° C. (4 torr). This example demonstrates that methyl 2-methoxyacrylate can be prepared using superatmospheric pressure.

EXAMPLE 6

In the manner of Example 2, methyl 2,2-dimethoxypropionate (92.4 g, 0.62 mol), was added to cinnamoyl chloride (125.8 g, 0.76 mol), quinoline (98.3 g, 118 ml, 0.76 mol), and powdered potassium hydroxide (2.0 g, 0.04 mol). The resulting mix was heated to 152° C. over one hour. After 15 minutes at 152° C., the reaction mix was cooled to 40° C. and transferred to a single-neck distillation flask. Vacuum distillation gave methyl 2-methoxyacrylate as a clear, colorless liquid (58.6 g, 81%); bp 67°-71° C. (35 torr); 24°-27° C. (2 torr); NMR, 3.64δ(s, 3H, —OCH$_3$); 3.82δ(s, 3H, CO$_2$CH$_3$; 4.64δ(d, 1H, =CH); and 5.38δ(d, 1H, =CH). This experiment demonstrates that co-product quinoline hydrochloride need not be removed from the reaction mix before product recovery. Thus, the addition and subsequent removal of solvent, e.g., toluene, can be eliminated.

EXAMPLE 7

Methyl 2,2-dimethoxypropionate (98.5 g, 0.66 mol) was combined with the cinnamoyl chloride (155.6 g, 0.93 mol), quinoline (120.4 g, 110.0 ml, 0.93 mol), and powdered potassium hydroxide (3.1 g, 0.056 mol). The resulting mixture was heated to 141° C. over two hours 15 minutes. Conversion of methyl 2,2-propionate was greater than 96%, and the reaction mix was a clear brown solution. Vacuum distillation gave methyl 2-methoxyacrylate as the initial overhead product, 24°-25° C. (4 torr): 65.6 g, 86%. This example demonstrates that solvent treating to precipitate quinoline hydrochloride need not be performed.

As can be seen from the foregoing examples the invention provides a method for producing high yields of 2-alkoxyacrylates not heretofore achieved. The following experiment, illustrative of the prior art processes, shows the expected yields from such prior art processes. Thus, α,β-unsaturated aliphatic esters were prepared using phosphorous pentoxide.

Methyl 2,2-dimethoxypropionate (14.8 g, 0.1 mol) was added at −5° C. to phosphorous pentoxide (15.3 g, 0.11 mol) at −5° C. under vacuum (90 torr). The reaction vessel was a four-necked flask equipped with thermometer, addition funnel, mechanical stirrer, and vacuum distillation apparatus. The pot contents were heated to 90° C. over 60 minutes and the volatiles distilled into a Dry Ice trap. Methyl 2-methoxyacrylate was detectable by NMR as one component of a mixture in the trap. The yield was less than 2%.

The reaction was repeated in the presence of pyridine (60 g, 0.76 mol) and again in the presence of quinoline (19.3 g, 0.15 mol). In both cases, methyl 2-methoxyacrylate was detectable as a minor component of a complex mixture. The yield was less than 5% in each case.

What is claimed is:

1. Process for preparing alkyl 2-alkoxyacrylate which comprises heating a reaction mixture comprising alkyl 2,2-dialkoxypropionate with a molar amount each of a heterocyclic amine and an organic carboxylic acid halide in the presence of a catalytic amount of an inorganic base.

2. Process according to claim 1, wherein the heating is effected at a temperature in about the range 50°-250° C.

3. Process according to claim 1, wherein the inorganic base is present in about the range 0.001–0.1 mol per mol of the heterocyclic amine and wherein the alkyl 2,2-dialkoxypropionate has the formula

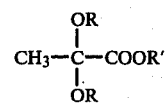

in which R is an alkyl group of 1 to 12 carbon atoms and R' is an alkyl group of 1 to 6 carbon atoms; the heterocyclic amine has the formula

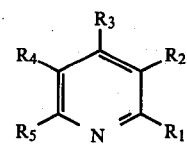

in which $R_1$, $R_2$, $R_3$, $R_4$ and $R_5$ are independently hydrogen or an alkyl group of 1 to 4 carbon atoms or in which any two adjacent R groups may represent a three- or four-carbon bridge forming a saturated or unsaturated five- or six-membered ring fused to the nitrogen-containing ring; the carboxylic acid halide has the formula

in which R is a hydrocarbyl radical of 1 to 12 carbon atoms and X is halogen.

4. Process according to claim 3, wherein the carboxylic acid halide is carboxylic acid chloride.

5. Process according to claim 4, wherein a small but effective amount of phenolic polymerization inhibitor is present to inhibit polymerization of the alkyl 2-alkoxyacrylate product.

6. Process according to claim 5, wherein heating is effected at a temperature in about the range 100°–200° C., the catalyst is present in an amount in about the range 0.005–0.01 mols per mol of heterocyclic amine, and the polymerization inhibitor is present in about the range of 0.01 to 1.0% of the alkyl 2,2-dialkoxypropionate.

7. Process according to claim 6, wherein the R group of the alkyl 2,2-dialkoxypropionate contains 1 to 6 carbon atoms.

* * * * *